(12) United States Patent
Doggett

(10) Patent No.: US 9,316,577 B1
(45) Date of Patent: Apr. 19, 2016

(54) OSCILLATORY PARTICLE ANALYZER

(71) Applicant: David E. Doggett, Berkeley, CA (US)

(72) Inventor: David E. Doggett, Berkeley, CA (US)

(*) Notice: Subject to any disclaimer, the term of this patent is extended or adjusted under 35 U.S.C. 154(b) by 0 days.

(21) Appl. No.: 14/796,735

(22) Filed: Jul. 10, 2015

(51) Int. Cl.
G01N 15/02 (2006.01)
G01N 15/14 (2006.01)
G01N 15/06 (2006.01)
B01F 11/00 (2006.01)

(52) U.S. Cl.
CPC ........ *G01N 15/1404* (2013.01); *B01F 11/0008* (2013.01); *G01N 15/1434* (2013.01); *G01N 15/1456* (2013.01); *B01F 11/0005* (2013.01); *B01F 11/0011* (2013.01); *G01N 15/0637* (2013.01)

(58) Field of Classification Search
None
See application file for complete search history.

(56) References Cited

U.S. PATENT DOCUMENTS

| | | |
|---|---|---|
| 2,531,529 A | 11/1950 | Price |
| 2,635,194 A | 4/1953 | Kellogg et al. |
| 3,470,377 A | 9/1969 | Febre et al. |
| 3,758,215 A | 9/1973 | Paruolo et al. |
| 3,760,184 A | 9/1973 | Brose |
| 3,766,489 A | 10/1973 | Rosenberg et al. |
| 3,858,851 A | 1/1975 | Ogle |
| 3,892,468 A | 7/1975 | Duguay |
| 3,894,806 A | 7/1975 | Remy et al. |
| 3,900,266 A | 8/1975 | Takahashi et al. |
| 3,956,616 A | 5/1976 | Knollenberg |
| 4,011,459 A | 3/1977 | Knollenberg et al. |
| 4,028,553 A | 6/1977 | Farcinade |
| 4,110,044 A | 8/1978 | Pettersson et al. |
| 4,402,612 A | 9/1983 | Alexander et al. |
| 4,576,477 A | 3/1986 | Corbet et al. |
| 4,623,252 A | 11/1986 | Hollenbeck |
| 4,804,273 A | 2/1989 | Tondello et al. |
| 4,871,251 A | 10/1989 | Preikschat et al. |
| 5,012,118 A | 4/1991 | Preikschat et al. |
| 5,037,559 A | 8/1991 | Schmitt |
| 5,164,597 A | 11/1992 | Lodder |
| 5,261,546 A | 11/1993 | Van Der Grift |
| 5,405,014 A | 4/1995 | Krieg et al. |
| 5,444,539 A | 8/1995 | van der Grift |
| 5,466,927 A | 11/1995 | Kohler et al. |
| 5,530,551 A | 6/1996 | Cantrall et al. |
| 5,653,537 A | 8/1997 | Ignatowicz et al. |
| 5,719,679 A | 2/1998 | Shimizu et al. |
| 5,812,270 A | 9/1998 | Hampton et al. |
| 5,870,190 A | 2/1999 | Unger |
| 5,900,933 A | 5/1999 | Schwartz et al. |
| 6,226,081 B1 | 5/2001 | Fantone et al. |
| 6,388,745 B2 | 5/2002 | Stevens et al. |
| 6,646,741 B1 | 11/2003 | Hoyte |

(Continued)

*Primary Examiner* — Kara E Geisel
*Assistant Examiner* — Amanda Merlino
(74) *Attorney, Agent, or Firm* — Faisal K. Abou-Nasr; Advent, LLP

(57) ABSTRACT

A low cost, compact, opto-mechanical system for particle analysis is disclosed. In embodiments of this disclosure, the system includes: a holder configured to rigidly secure a container that contains a liquid sample; an actuator configured to repetitively rotate the holder N degrees in a first direction and M degrees in a second direction different from the first direction, wherein N and M are real numbers greater than zero; a radiation source configured to generate a beam of radiation, the radiation source being rigidly attached to the holder; and a detector configured to receive radiation that is at least one of scattered, reflected, diffracted, refracted, or radiated from one or more particles within the liquid sample in response to the beam of radiation being incident upon the one or more particles.

19 Claims, 11 Drawing Sheets

(56) References Cited

U.S. PATENT DOCUMENTS

| | | |
|---|---|---|
| 6,765,675 B2 | 7/2004 | Dragotta |
| 6,809,820 B2 | 10/2004 | Snelling et al. |
| 6,966,994 B2 | 11/2005 | Berns et al. |
| 7,012,242 B2 | 3/2006 | Tarozzi et al. |
| 7,064,309 B2 | 6/2006 | Wagoner et al. |
| 7,148,961 B1 | 12/2006 | Ringlien |
| 7,214,925 B2 | 5/2007 | Wagoner et al. |
| 7,377,151 B1 | 5/2008 | Magee |
| 7,731,414 B2 * | 6/2010 | Vincent ............... B01F 11/0002 210/222 |
| 8,224,196 B2 | 7/2012 | Oh |
| 8,670,120 B2 | 3/2014 | Brunel |
| 2005/0185180 A1 * | 8/2005 | Moore ................... B24B 37/04 356/343 |
| 2014/0185407 A1 | 7/2014 | Yang |

* cited by examiner

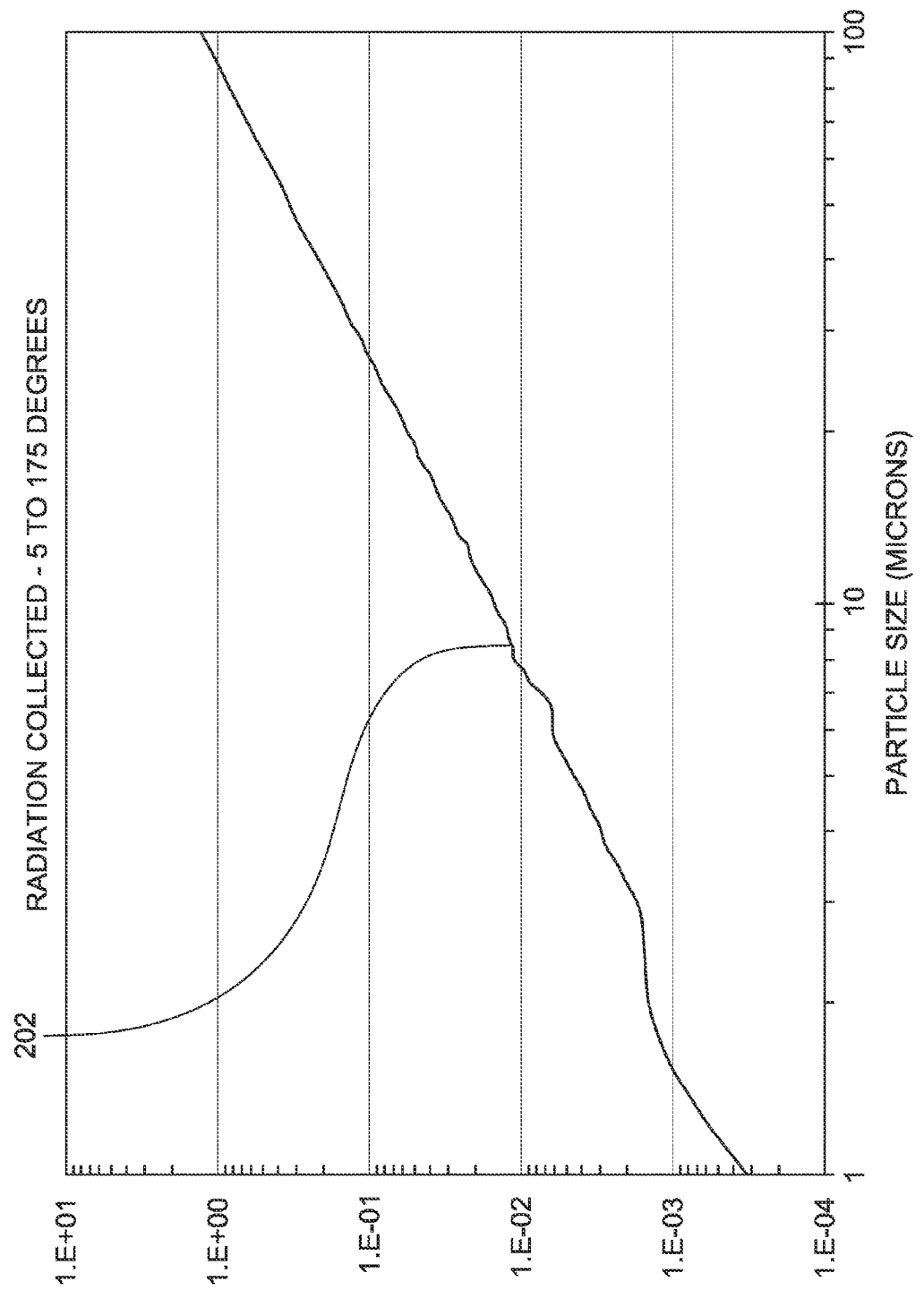

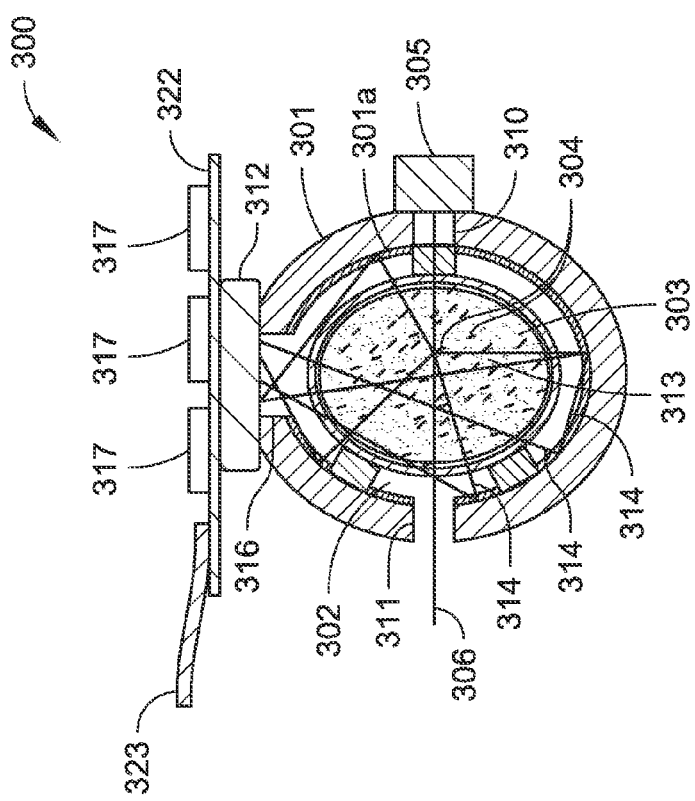
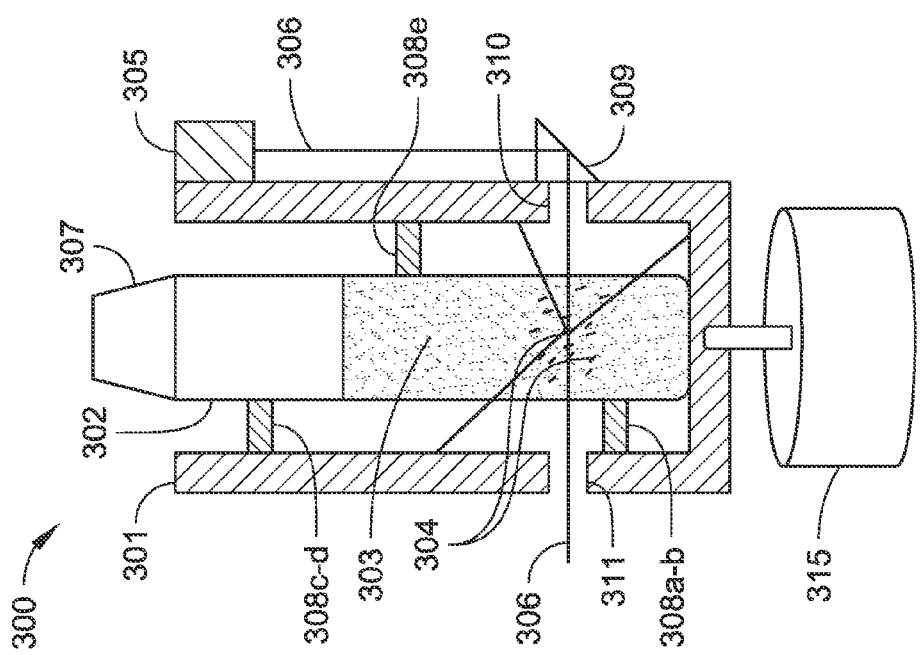
FIG. 3B
FIG. 3A

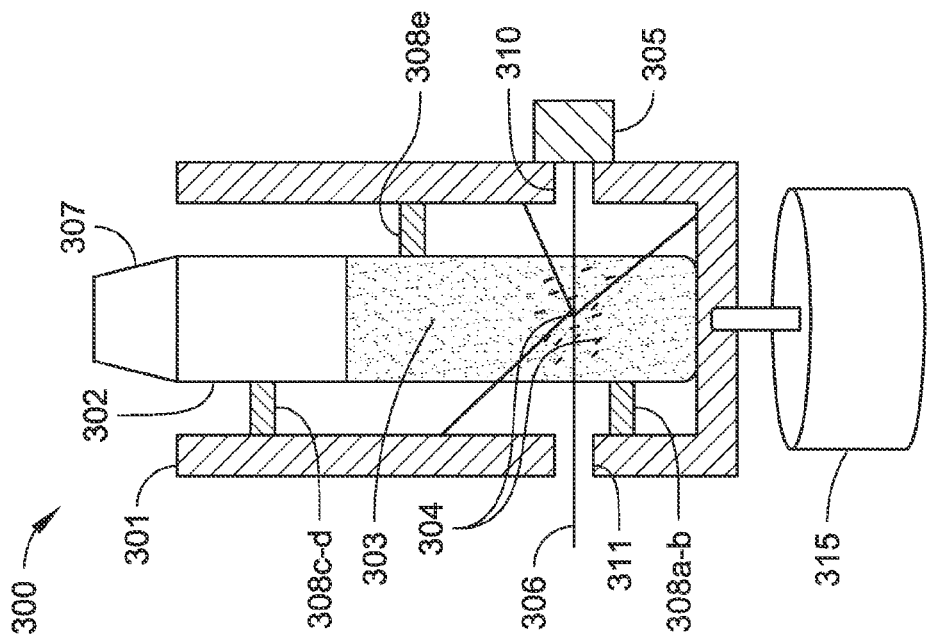
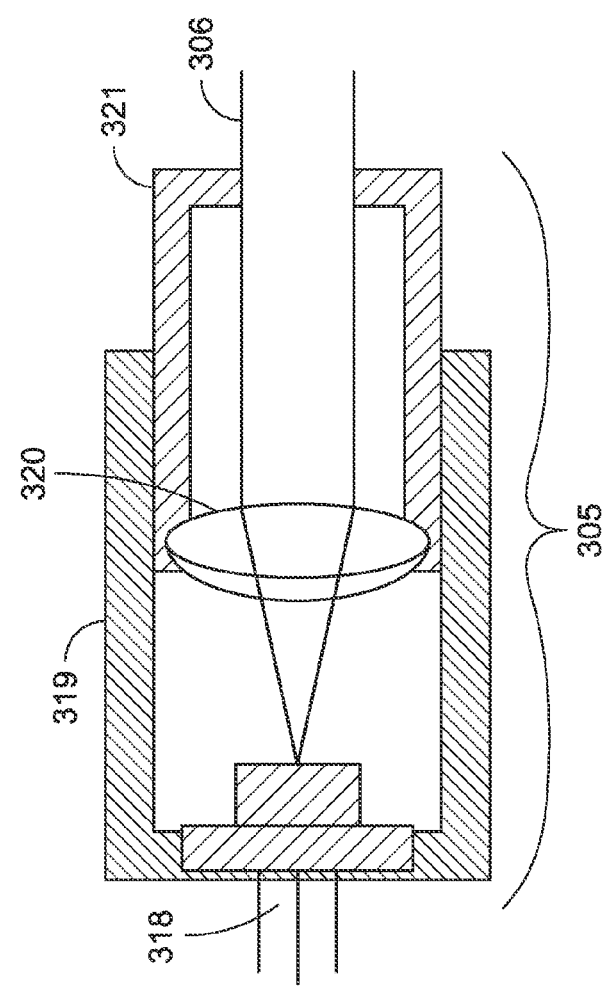
FIG. 3D
FIG. 3C

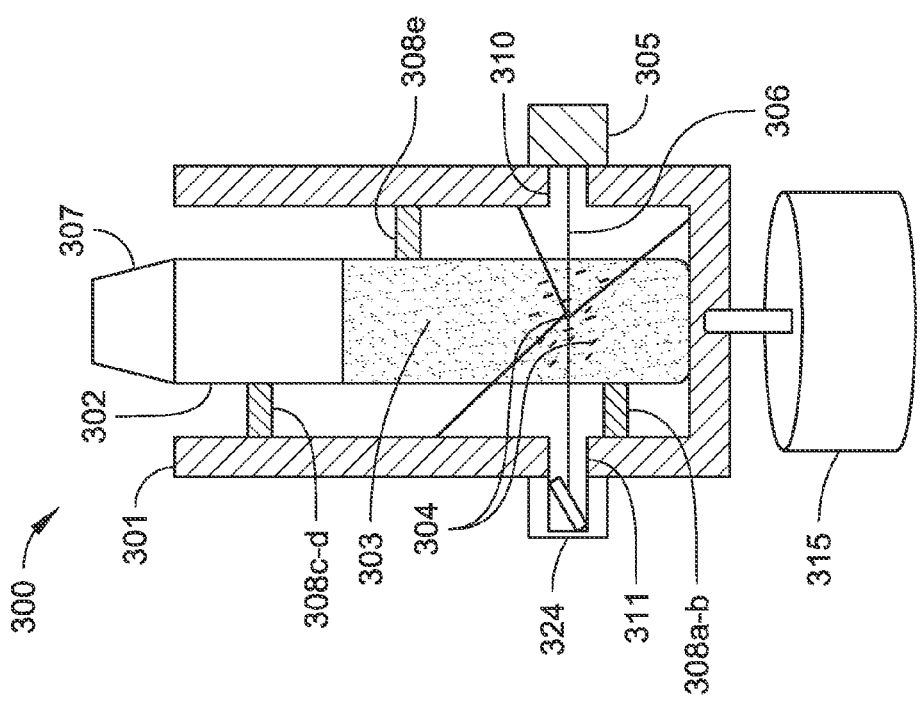
FIG. 3E
FIG. 3F

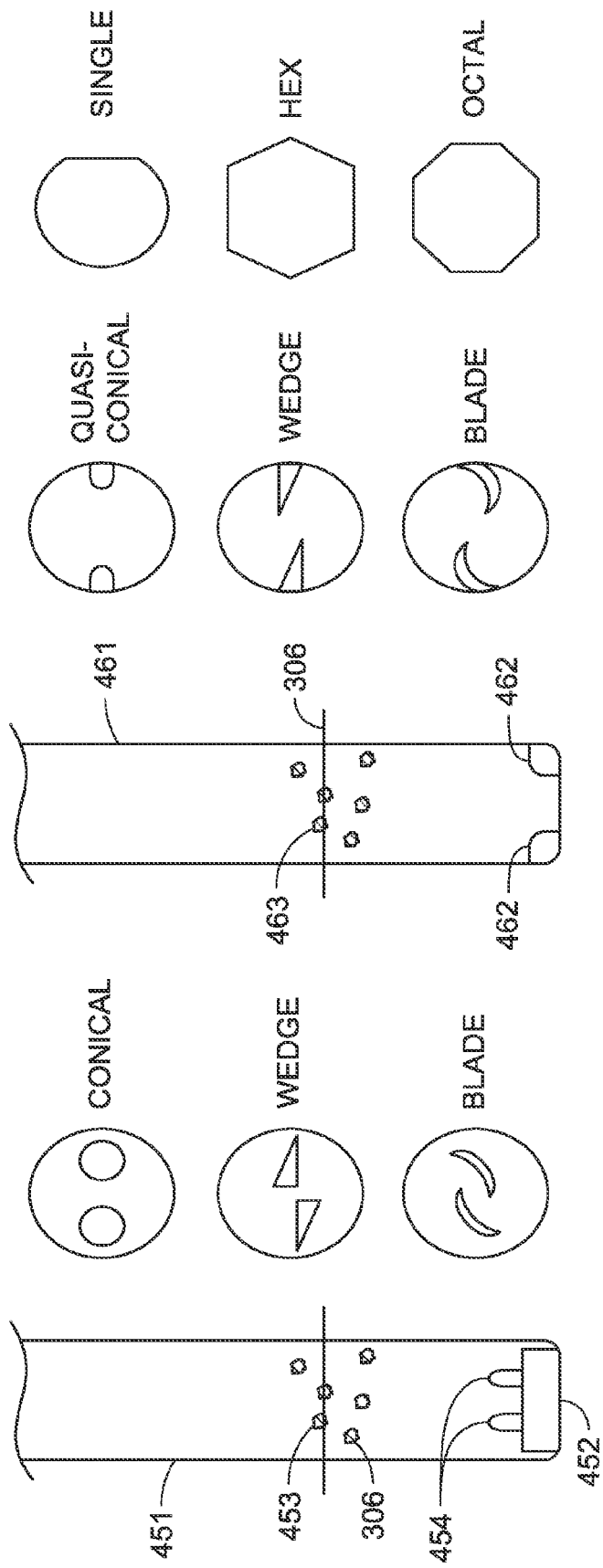

OSCILLATORY PARTICLE ANALYZER

TECHNICAL FIELD

The present disclosure relates to particle analysis, and more particularly, to a system and method for: scanning a radiation probe beam through a liquid sample volume and collecting radiation that is scattered, reflected, diffracted, refracted, and/or radiated from particles suspended in the liquid.

BACKGROUND

Systems or devices used to determine characteristics (e.g., number, size distribution, or classification) of small particles in various liquids are generally referred to as particle analyzers. Optical particle analyzers measure particles by irradiating particles flowing in a flow cell or contained in a sample container and detecting and processing radiation scattered from said particles. One particularly useful type of particle analyzer utilizes a laser beam to probe a liquid and produce scattered radiation from suspended particles therein. Radiation scattered by small particles within the sample liquid is detected and electrically processed to produce a measurement of one or more parameters of particles present in the sample liquid. Examples of optical analyzer systems are disclosed in U.S. Pat. No. 4,804,273 to Tondello et al., U.S. Pat. No. 4,623,252 to Hollenbeck, U.S. Pat. No. 3,956,616 to Knollenberg, and U.S. Pat. No. 3,858,851 to Ogle, each of which is incorporated herein by reference.

FIG. 1A illustrates a particle analyzer with an optical system similar to that disclosed in U.S. Pat. No. 3,858,851, where the optical system is shown to include: laser 101, laser beam 102, first lens 103, angled optical flat 104, transparent container 105 filled with liquid 106 containing particles 107, optical obstacle 108, second lens 109, photo detector 110, and processing electronics 111. Angled optical flat 104 is rotated about the axis of laser beam 102 producing an offset rotary beam which imparts a relative motion between laser beam 102 and particles 107 within liquid filled transparent container 105. Light scattered from particles 107 is collected by second lens 109 and presented to photo detector 110. Light contained in laser beam 102, not scattered by particle 107, is stopped by obstacle 108 and is absorbed. Some shortcomings of this configuration are that: 1) transparent container 105 needs to be of high optical quality because laser beam 102 traverses a circular path over and through wall 112; 2) transparent container 105 needs to be large in diameter so scan dependent scattering at the surface of container 105 is spatially removed from particle scattering in sample volume 114; 3) the entire optical system needs to be long so reasonable focal length lenses can be utilized and reasonable optical sample volume sizes can be produced; and 4) the collection of scattered light from a limited range of angles defined by the collection cone of lens 109 produces a multi-valued relationship of collected scattered intensity to particle diameter (as shown in FIG. 2A).

FIG. 1B illustrates a particle analyzer with an optical system to that disclosed in U.S. Pat. No. 4,804,273, where the optical system is shown to include: laser 151, laser beam 152, first lens 153, motor means 154, transparent container 155 filled with liquid 156 containing particles 157, collection means 159, photo detector 160, and processing electronics 163. Initially, motor means 154 rotates many full revolutions which causes transparent container 155 to rotate, thereby causing liquid 156 containing particles 157 to rotate. When transparent container 155's rotation is stopped, liquid 156 containing particles 157 continues to rotate resulting in a continued relative motion between laser beam 152 and particles 157 within liquid filled transparent container 155. Scattering of laser beam 152 by particles 157 is detected by photo detector 160. This configuration has two significant drawbacks. 1) The rotary motion of transparent container 155 filled with liquid 156 containing particles 157 will tend to concentrate particles 157 in the center of the liquid filled transparent container 155, the so called 'tea leaf paradox.' This effect is explained by Albert Einstein in *The Cause of the Formation of Meanders in the Courses of Rivers and of the So-Called Baer's Law*, Die Naturwissenschaften, Vol. 14, 1926. 2) As the liquid rotates, the laser beam only probes a single cylindrically shaped annular volume of liquid within the container. Since the particles, in general, rotate with the liquid in a circle about the axis of the sample container, for multiple rotations of the liquid contents of the sample container there will be multiple measurements of the same liquid volume, leading to limited statistics with regard to the number and sizes of particles within the liquid sample.

SUMMARY

The present disclosure describes a particle analyzer that utilizes a radiation probe beam to interact with small particles suspended in a liquid contained in a sample container that is transparent to the wavelength of radiation employed. The disclosed particle analyzer utilizes a property of a liquid in a sample container (e.g., a cylindrical or substantially cylindrical sample container such as a vial), whereby when the sample container is rotated about its central axis the liquid within the sample container remains relatively stationary for a period of time. As the sample container holding the liquid is initially rotated there is established a relative motion between the structure of the sample container and the substantially stationary liquid therein. If the sample container is securely placed in a sample container holder, and a radiation source is securely mounted to the structure of the sample container holder, and its radiation is directed as a radiation probe beam through a substantially transparent wall of the sample container and thence into the liquid in the sample container, then when the sample container holder/sample container system is rotated there will initially be a relative motion between the rotating radiation source's beam and the stationary liquid contained within the sample container. This relative motion will, in general, be maintained for a plurality of revolutions of the sample container holder depending on the viscosity of the liquid.

If the rotary motion of the sample container holder and rigidly attached sample container were to stop well before the contained liquid's motion matches the sample container's rotary motion and the sample container holder were to reverse its rotary motion, this reverse rotary motion would again establish a relative motion between the rotating radiation source's probe beam and the substantially stationary liquid contained within the sample container. If the rotary motion were to periodically reverse its motion there would continually be reestablished relative motion between the sample container's liquid and the radiation source without any substantial rotary motion of the liquid in the sample container.

This oscillatory movement of the sample container holder and thereby of the securely held sample container will produce an intermittent, repeatable relative motion between the radiation probe beam and the liquid within the sample container without imparting any significant movement to the liquid contained therein. The oscillatory movement is provided by an actuator (e.g., motor or servo) mounted in such a way that its motive power can be used to rotate the sample container holder substantially around its central axis. In embodiments, the actuator is coupled to the sample container holder in such a way that it is capable of producing rotary motion in both a clockwise and a counterclockwise direction.

The rate at which the sample container is rotated and the number of cycles of rotation in a first direction and then in a second direction will be determined by the parameters of the system constructed and by the nature of the liquid sample within the sample container and by the particle statistics desired. For a large diameter sample container a slower rate of rotation will be sufficient to produce the required relative motion between the probe beam and the particles contained within the sample liquid. For a viscous liquid a faster rotation rate will be required. From the parameters of the radiation beam the volume of the liquid being probed as the radiation beam transits the interior of the sample container can be determined. From that volume determination together with knowledge of the angle of rotation in a first direction and subsequently in a second direction of the sample container, the total liquid volume probed for each rotation cycle can be determined. From that information together with the desired total probe volume of liquid scanned the number of cycles of rotation can be determined.

For instance, in some embodiments, the probe beam diameter will be 100 microns, the interior diameter of the sample container will be 20 mm and the rotation angle of the sample container in a first direction of 180 degrees and the rotation in the second direction of 180 degrees. In this instance the total volume probed will be 63 cubic millimeters for a complete scan cycle. If it is desired to scan one cubic centimeter which equals 1000 cubic millimeters a series of sixteen complete scan cycles may be required. In this instance if the liquid in the sample container is water a reasonable time for a complete scan cycle might be one second. This a nominal number and a scan time of twice one second or a scan time of one half one second will work just as well. Scan times in excess of two seconds or shorter than one half second will work depending on other parameters of the particle analyzer system such as detector rise times, electronic bandwidth, motive power requirements, and so forth.

The particle analyzer includes a detector, which in a likewise manner to the radiation source, is attached to the structure of the sample container holder. The sample container holder includes an aperture for radiation that is scattered, reflected, diffracted, refracted, and/or radiated from the particles suspended in the sample container's liquid to reach the detector. In some embodiments, the aperture is located approximately 90 degrees from the probe beam's entry and exit points about an outer edge of the sample container holder.

Some embodiments of the disclosed system can have a detector placed at different locations than that described above or may have multiple detectors placed at many different angles or locations with respect to the probe beam. The radiation probe beam can be a beam containing more than one wavelength of radiation. The detectors can be detectors engineered to be sensitive to the different wavelengths of radiation, and there may be multiple electronic processing channels to recover information from the multiple probe beam wavelengths and multiple associated detectors.

In some embodiments, the sample container holder is a hollow cylinder, closed at one end. The interior of the sample container holder's structure can be coated with a highly, diffusely reflective substance to the wavelength of the probe beam. As such, scattered radiation from small particles within the sample liquid may be reflected multiple times from the highly, diffusely reflective walls of the interior of the sample container holder and a portion of that radiation will enter the aperture opening and thence proceed to the detector. Because the interior of the sample container holder is substantially enclosed and highly diffusively reflective, the interior can be characterized as an integrating cylinder, collecting substantially all of the various angles of scattered radiation from the small suspended particles. Because substantially all of the various scattering angles are collected and presented to the detector, the relationship of scattering intensity to particle diameter is of a monotonic nature. That is, there exists no multi-valued relationship of collected scattered intensity to particle diameter.

In some embodiments, the detector comprises a silicon diode optical detector that produces a current output in response to incident scattered radiation from particles in the sample liquid. Detectors such as photomultiplier detectors and other detectors known to someone skilled in the art may be substituted. A transimpedance amplifier can be used to convert the current from the optical detector into a voltage. An analog-to-digital converter (ADC) can periodically sample and convert the voltage from the transimpedance amplifier into a digital code that can be sent from the particle analyzer sensor assembly to other electronics (e.g., a computer processor or microcontroller) for further signal processing to determine one or more characteristics of the scanned particles within the liquid sample based upon the detected radiation. For example, electronic signals that are associated with the detected radiation can be processed to determine a quantity of particles, size distribution of the particles, particle type(s), classification(s), physical properties, and so forth.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 2B shows a graph of calculated pulse signal height vs. particle diameter for a particle analyzer constructed in accordance with an embodiment of the present disclosure.

FIG. 3A is a cross-sectional side view of a particle analyzer sensor assembly constructed in accordance with an embodiment of the present disclosure.

FIG. 3B is a cross-sectional top view of a particle analyzer sensor assembly constructed in accordance with an embodiment of the present disclosure.

FIG. 3C shows a diode laser assembly constructed in accordance with an embodiment of the present disclosure.

FIG. 3D is a cross-sectional side view of a particle analyzer sensor assembly constructed in accordance with an embodiment of the present disclosure.

FIG. 3E is a cross-sectional side view of a particle analyzer sensor assembly constructed in accordance with an embodiment of the present disclosure.

FIG. 3F shows beam dump configurations in accordance with various embodiments of the present disclosure.

FIG. 4E shows a sample container constructed in accordance with an embodiment of the present disclosure, wherein at least one insert is secured to an inner surface of the sample container.

FIG. 4F shows insert configurations for a sample container constructed in accordance with an embodiment of the present disclosure.

FIG. 4G shows a sample container constructed in accordance with an embodiment of the present disclosure, wherein one or more protuberances are formed from one or more portions of the bottom and/or side of the sample container.

FIG. 4H shows insert or protuberance configurations for a sample container constructed in accordance with an embodiment of the present disclosure.

FIG. 4I shows exemplary alternative form factors for a sample container constructed in accordance with an embodiment of the present disclosure.

DETAILED DESCRIPTION

Overview

Figure 1B:
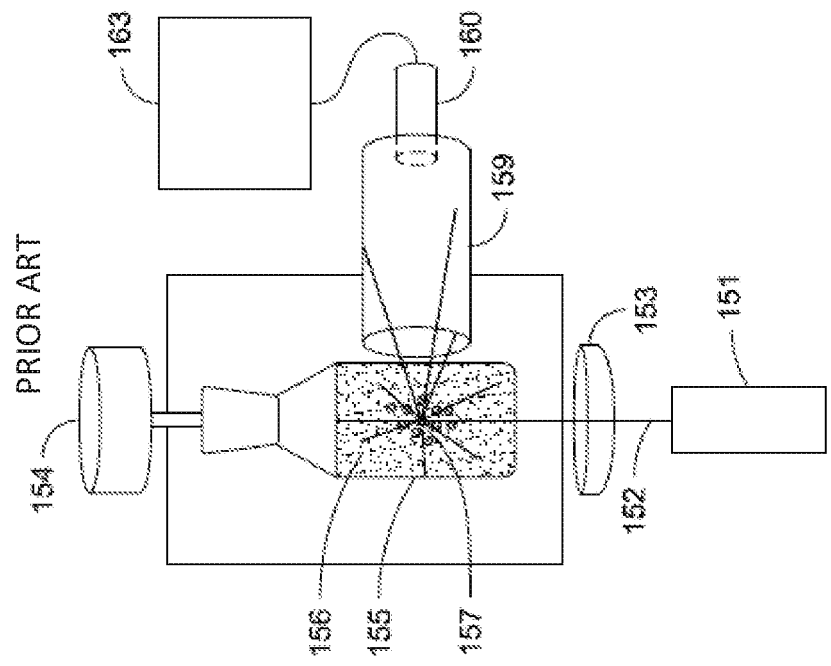
FIG. 1B illustrates an example of a particle analyzer.
Figure 1A:
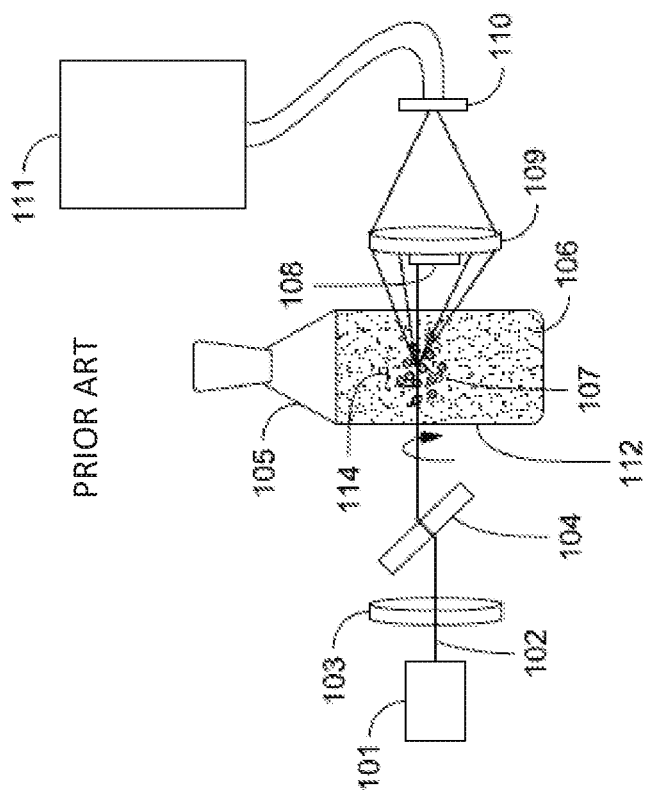
FIG. 1A illustrates an example of a particle analyzer.

The present disclosure describes a system and methodology that leverage a property of a sample liquid in a sample container (e.g., a cylindrical or substantially cylindrical container), whereby when the sample container is rotated about a central axis of the sample container, the sample liquid within the container remains relatively stationary for a period of time. In order to achieve rotary motion of the sample liquid inside the sample container that matches the rotary motion of the sample container, multiple rotations of the sample container must ensue depending on viscosity of the sample liquid. Therefore, as the sample container is initially rotated there exists a relative motion between the sample container's wall structure and the substantially stationary sample liquid therein. If the sample container is placed inside a structure that can hold the sample container securely and if this structure is allowed to rotate in response to a motive force supplied by an actuator (e.g., motor or servo), it is possible to rotate the sample container holder and thereby the sample container in a clockwise and then a counter clockwise manner. In that case, there is alternately a relative motion between the sample container/sample container holder system with respect to the liquid within one direction and subsequently a relative motion between the sample container/sample container holder system with respect to the liquid within in the opposite direction; and yet, the liquid inside the sample container will remain substantially stationary.

In embodiments of the present disclosure, a radiation source is securely mounted to the exterior region or surface of a sample container holder, and its radiation beam is directed via one or more optical elements from the radiation source to a point where the radiation beam can be directed through an input aperture in the sample container holder's wall and into the securely held transparent sample container and thence into the sample liquid within the container as a radiation probe beam. For example, the beam can be directed along a path via one or more optical elements having fixed positions relative to the sample container, such as optical elements including, but not limited to, lenses, prisms, fiber optics, mirrors, diffractive elements, and the like. In some embodiments, the radiation source can alternatively be secured within an interior region of the sample container holder. In such a case, no input aperture in the wall of the sample container holder's wall is necessary. Additionally, the radiation beam does not necessarily need to be directed into the container via one or more optical elements. Instead, the radiation source can be positioned such that the radiation beam is directed from the radiation source into the container without additional optics. Because the radiation source is firmly attached to the sample container holder, when the sample container holder and its securely held sample container is rotated there will be no relative motion between the probe beam and the sample container holder; and yet, there will be a relative motion between the radiation probe beam and the liquid containing suspended particles within the sample container. This relative motion would be maintained for several revolutions of the sample container depending on the viscosity of the liquid. If, however, the rotary motion of the sample container holder and rigidly attached sample container were to stop well before the rotary motion of the contained liquid matched the sample container's rotary motion, and if the sample container holder and the rigidly attached sample container were to reverse their rotary motion, this reverse rotary motion will again establish a relative motion between the radiation source and the liquid contained within the sample container.

The rotary motion periodically reverses and thereby continually reestablishes relative motion between the sample container's liquid and the radiation source after a rotary motion of approximately 180 degrees (one half revolution) of the sample container holder and its rigidly attached sample container. In this regard, the sample container can be repetitively rotated N degrees in a first direction and M degrees in a second (opposite) direction to achieve oscillatory scanning of the sample liquid. Even with a brief rotation (e.g., 180 degrees), the radiation probe beam can perform a complete scan of a single measurement plane within the sample liquid. The angle of motion in the clockwise and counter clockwise directions can be of any angle that satisfies the requirements of a particular system design. For example, M and N can each be less than or equal to 180 degrees, or 360 degrees, or 720 degrees, or any other suitable rotation for maintaining a relative motion between the radiation probe beam and the liquid within the sample container. The rate of rotation reversal can be varied over a wide a latitude. Some embodiments can have the time between reversals range from as long as 10 seconds or more to as short as 0.01 seconds or less.

Example Implementations

Figure 4A:
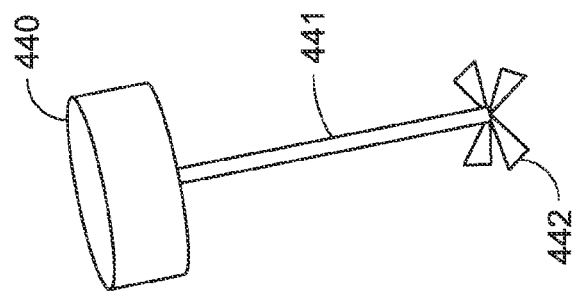
FIG. 4A shows a sample container constructed in accordance with an embodiment of the present disclosure.
Figure 4B:
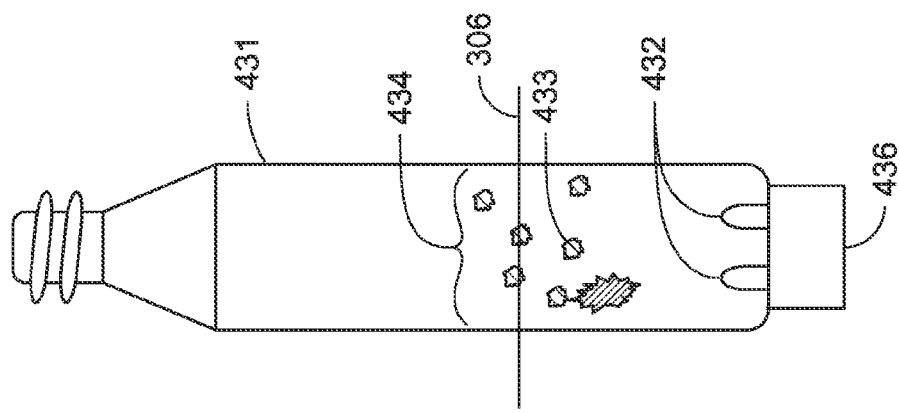
FIG. 4B shows protuberance configurations for a sample container constructed in accordance with an embodiment of the present disclosure, wherein one or more protuberances are formed from one or more portions of the sample container.
Figure 4C:
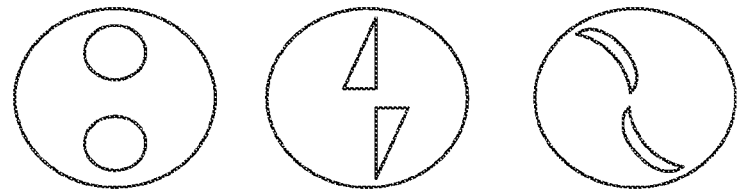
FIG. 4C shows a sample container constructed in accordance with an embodiment of the present disclosure, wherein an endcap is affixed to a bottom of the sample container.
Figure 4D:
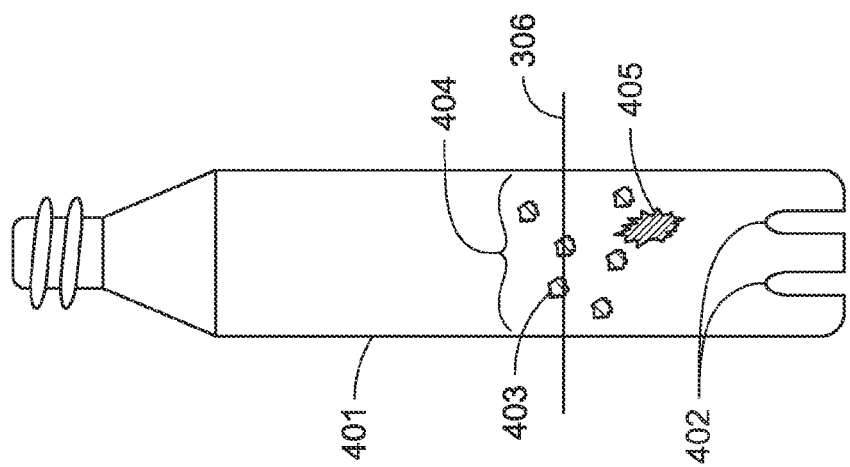
FIG. 4D shows a top cap configuration with stirring assembly for a sample container constructed in accordance with an embodiment of the present disclosure.
Figure 5:
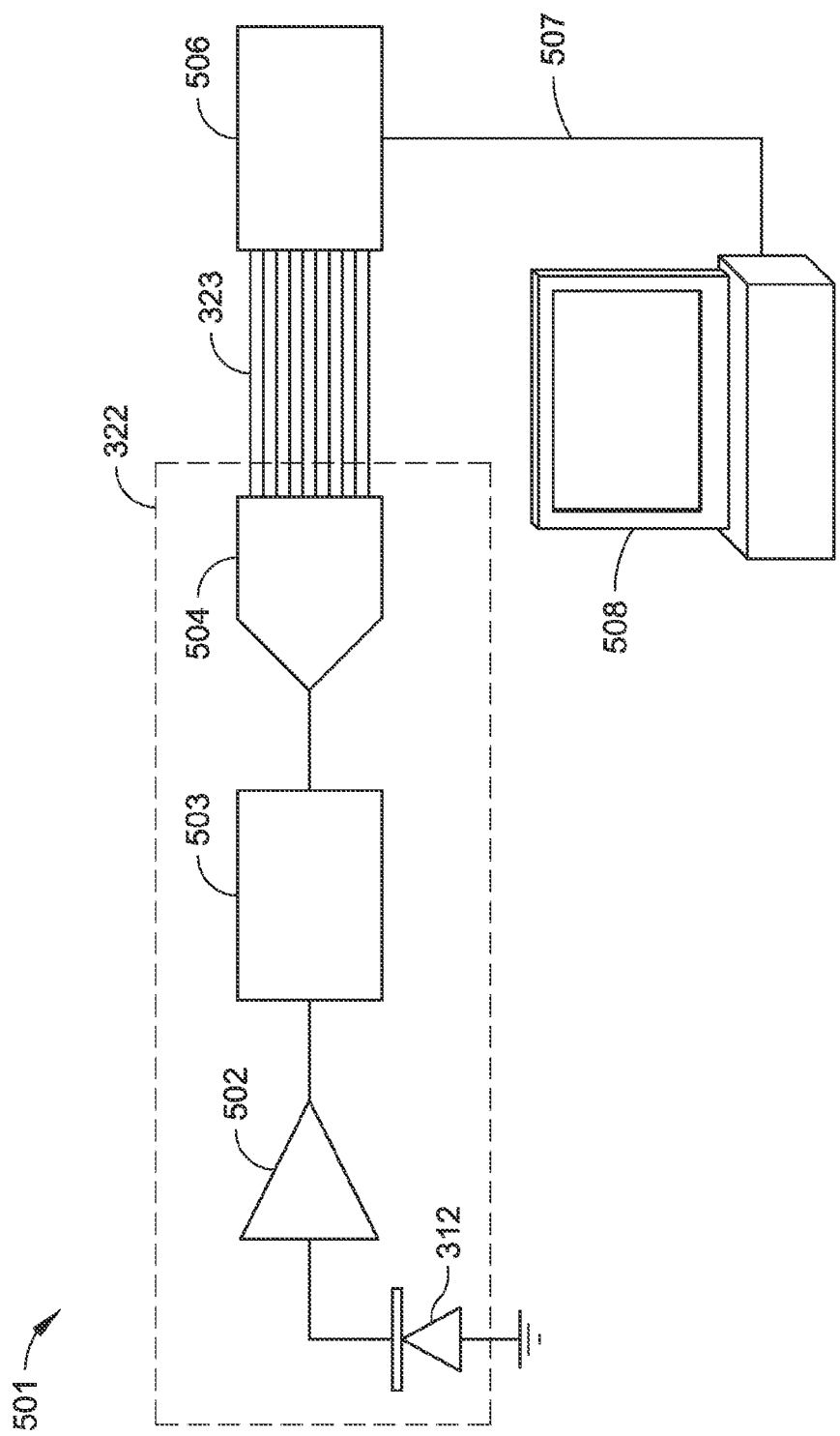
FIG. 5 shows a block diagram of a data acquisition and processing system for a particle analyzer constructed in accordance with an embodiment of the present disclosure.

FIGS. 3A through 4I illustrate various elements of a particle analysis system (sometimes referred to herein as a particle analyzer) shown schematically in FIG. 5, in accordance with various embodiments of this disclosure. Those skilled in the art will appreciate that the embodiments illustrated in the drawings and/or described herein may be fully or partially combined to result in additional embodiments. Accordingly, the illustrated and described embodiments should be understood as explanatory and not as limitations of the present disclosure.

In FIG. 3A, an embodiment of a particle analyzer sensor assembly 300 is shown to include a sample container holder 301 that surrounds and rigidly secures a sample container 302 which contains a liquid sample 303 having suspended particles 304 therein. Rigidly attached to sample container holder 301 is a radiation source 305. In some embodiments, radiation source 305 is a laser source, such as a diode laser radiation source. Diode lasers of various wavelengths and output powers may be suitable depending on the application. For example, a suitable diode laser can be model no. DL4140-001S available from Newport, Corp., 1791 Deere Avenue, Irvine, Calif. 92606.

A detailed embodiment of radiation source 305 is shown in FIG. 3C, which can include a diode laser 318, a diode laser holder 319, a collecting lens 320, and a collecting lens holder 321. Collecting lens 320 can be any of a variety of collecting/collimating lenses. For example, a suitable lens can be part number 302-0355-780 which can be purchased from Optima Precision, Inc., 775 SW Long Farm Road, West Linn, Oreg. 97068, U.S.A. Collecting lens 320 may be adjustable in its axial position with respect to diode laser 318 so that the collected radiation from diode laser 318 can be appropriately concentrated within sample container 302. After this adjustment, collecting lens holder 321 can be firmly attached to diode laser holder 319 to restrict further movement. This attachment can be accomplished by any of a number of adhesives or the like known in the art. The waist diameter of the concentrated beam of radiation from radiation source 305 will be dependent upon the application. For instance, a small concentrated beam waist would provide high energy density and can be applicable for detecting small suspended particles. For larger particles, a larger beam waist may be required to prevent total beam obscuration during particle transit through the beam. Application dependent decisions of this nature will affect the selection of diode laser 318, collecting lens 320 and the placement of radiation source 305 on sample container holder 301. Such application dependent decisions would be apparent to one skilled in the art of optical system design.

In some embodiments, radiation source 305 is positioned such that radiation output beam 306 is parallel to the axis of sample container holder 301. Radiation source 305 can be secured to an exterior portion of sample container holder 301. Radiation beam 306 can be directed by an optical element 309 (e.g., a prism, mirror, diffractive element, fiber optic, or the like) through an input aperture 310 formed in the side of sample container holder 301 and into sample liquid 303 contained in sample container 302. Alternatively, radiation beam 306 can travel directly from radiation source 305 into sample container 302. For example, radiation source 305 can be secured within sample container holder 301 or externally secured such that it is oriented into sample container holder 301 (e.g., as shown in FIG. 3D).

In some embodiments, sample container 302 can be a glass vial. Glass vials suitable for use as a sample container can be purchased at any laboratory supply house such as Cole-Parmer, ThermoFisher Scientific and Wheaton. Other sample containers including plastic sample containers can also be utilized. The sample container need not have a readily removable lid as shown in FIG. 3A. In some embodiments, sample container 302 can be a 30 milliliter glass vial, Part Number 14-955-320, sold by Thermo Fisher Scientific Inc. 300 Industry Drive, Pittsburgh, Pa. 15275.

Sample container 302 can be rigidly attached to sample container holder 301 by holding elements (e.g., elements 308a through 308e). Any convenient method for retaining the sample container can be used. For example, elements 308a through 308e can be screws, clamps, or any other fasteners known to the art. Radiation beam 306 leaves radiation source 305, is directed toward the interior of sample container holder 301 by optical element 309 and enters an interior region of the sample container holder through aperture 310 in the side of sample container holder 301. Once in the interior of sample container holder 301, radiation beam 306 goes through a transparent surface of sample container 302 and proceeds through sample liquid 303. Within this liquid are particles 304, some of which will be within the path of radiation beam 306. Radiation beam 306 then exits the interior of sample container holder 301 through an output aperture 311. As shown in FIG. 3E, the particle analyzer sensor assembly 300 can further include a beam dump 324 placed adjacent to output aperture 311 and configured to receive radiation beam 306 to stop radiation beam 306 from continued travel. In some embodiments, beam dump 324 can be formed by radiation absorbing substrate, such as a black glass substrate, black paint, black tape, or any other substrate capable of absorbing most wavelengths of light or any other applied radiation. In some implementations of beam dump 324, an absorbing glass substrate can be oriented at a Brewster angle (sometimes referred to as a polarization angle) within the exit radiation beam, where the radiation beam will be transmitted into and absorbed by the substrate with substantially no reflection. FIG. 3F shows additional examples of beam dump 324 in accordance with various embodiments. Additional form factors or structural configurations can also be implemented without departing from the scope of this disclosure. Beam dump 324 can alternatively be implemented on an inner surface of sample container holder 301 in the form of black tape, black paint, or a surface mounted substrate on the inner surface of sample container holder 301. In such a configuration, sample container holder 301 will not require an output aperture.

Referring to FIG. 3B, showing a top view of the particle analyzer sensor assembly 300, a detector 312 can be seen mounted to sample container holder 301. Detector 312 can be any of a wide variety of detectors known to one skilled in the art of optical system design. It is desirable for the detection area of detector 312 to be relatively large in order to better collect energy from radiation that is scattered, reflected, diffracted, refracted, and/or radiated from particles 304 suspended in sample liquid 303. For example, a detector that is suitable for this purpose is part number S1337-1010BR from Hamamatsu Corporation, 360 Foothill Rd, Bridgewater, N.J. 08807. Radiation beam 306 from radiation source 305 can be scattered, reflected, diffracted, refracted, and/or radiated by a particle within the diameter of radiation beam 306. Radiation 313 that is scattered, reflected, diffracted, refracted, and/or radiated from particles 304 falls incident upon integration and collection surface 301a (or a plurality of surfaces 301a). In some embodiments, surface 301a comprises a prepared interior surface of sample container holder 301, where radiation that is scattered, reflected, diffracted, refracted, and/or radiated from one or more particles within the diameter of radiation beam 306 is reflected or redirected from the interior surface of sample container holder 301 at a plurality of points until the radiation is received by detector 312. The effect of this integration and collection homogenizes radiation that is scattered, reflected, diffracted, refracted, and/or radiated from one or more particles in the radiation beam so that the radiation is collected by detector 312 from most (e.g., nearly all) scattering angles. Radiation 314, diffusively reflected from surface 301a, fills the interior of sample container holder 301 and a portion of that radiation is directed through aperture 316 and thence to detector 312 to produce a signal level with an improved relationship of particle diameter to particle size over that of other particle analyzers known to the art. The signal from detector 312 is then amplified and processed by electronics 317 mounted on PCB 322.

In some embodiments, the interior surface 301a of sample container holder 301 is prepared by coating it with a highly reflecting substance to enhance the intensity of the radiation entering aperture 316 and thence to detector 312. For example, a suitable substance for this purpose would be White Reflectance Coating 6080 manufactured by Labsphere, Inc., 231 Shaker Street, North Sutton, N.H. 03260. The integration of scattered radiation from the interior surface of sample container holder 301 tends to smooth out variations in the scattered light from the suspended particles by incorporating most of the different intensity lobes of radiation presented to detector 312. The shape of the integrating volume can be shapes other than cylinders. For example, a sphere, a cube, or pancake like structure can be substituted for the cylindrical structure of sample container holder 301 shown in FIGS. 3A, 3B, 3D, and 3E.

Figure 2A:
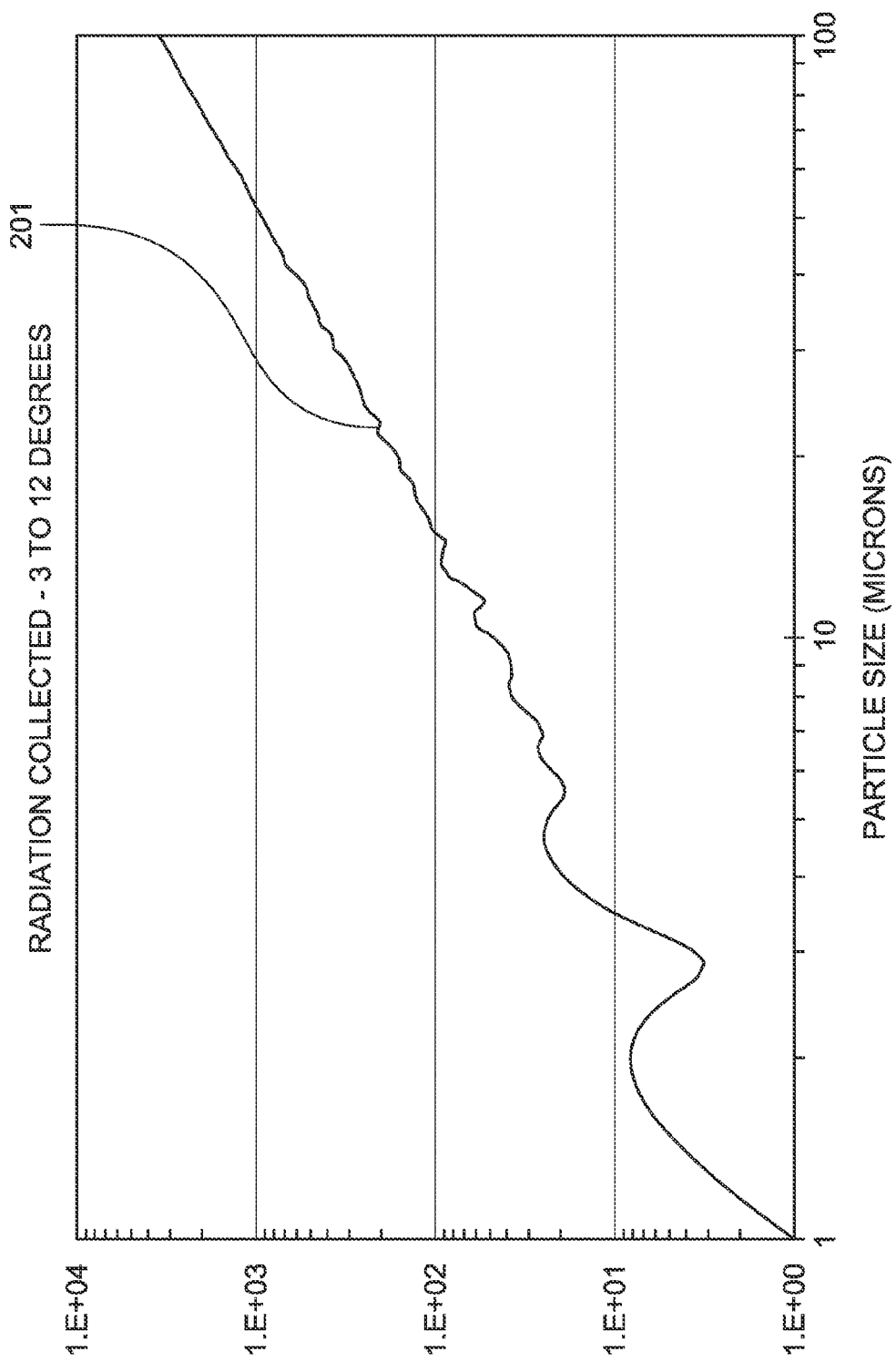
FIG. 2A shows a graph of calculated pulse signal height vs. particle diameter for an example particle analyzer.

FIGS. 2A and 2B show the calculated scattered radiation intensity of varying particle size for two different radiation collection systems. Line 201 of FIG. 2a shows the relationship between scattered radiation intensity and particle diameter for a particle analyzer such as the one disclosed in U.S. Pat. No. 3,858,851. This line shows that the relationship of scattering intensity to particle diameter is multi-valued for some particle sizes. That is, the scattered radiation intensity for one particle diameter may be identical to the scattered radiation intensity of a different particle diameter. This makes unique identification of particle diameter impossible in those instances.

Line 202 of FIG. 2B shows the relationship between scattered radiation intensity and particle diameter for a detection system of particle analyzer sensor assembly 300. Line 202 of FIG. 2B shows that the relationship between scattered radiation intensity and particle diameter is not multi-valued. That is, the scattered radiation intensity for one particle diameter is unique and of a different value to every other particle diameter. This makes unique identification of particle diameter possible.

In operation, an actuator 315 (e.g., motor or servo) is energized so as to impart an oscillatory motion on sample container holder 301 with its rigidly attached laser source 305 and rigidly attached sample container 302 about an axis substantially parallel to the central axis of sample container 302. This oscillatory motion creates a continuous train of temporally spaced apart periods of relative motion between radiation beam 306 and sample liquid 303 and its suspended particles 304. Actuator 315 can be connected to sample container holder 301 indirectly by belts, gears, transmissions, cam mechanisms or the like; or in some embodiments, sample container holder 301 is connected directly to the output shaft of actuator 315. Actuator 315 can be, for example, a stepper motor that is programmed to directly produce the desired motion. Any of a variety of stepper motors can be used and should be known to one skilled in the art of motion control. For example, a stepper motor that is suitable can be part number 4018M-04 available from Lin Engineering, 1990 Russell Avenue, Santa Clara, Calif. 95054. Any of a number of motors can be used for this purpose, such as brushed or brushless DC motors, air motors, or hydraulic motors.

It has been found that a rotation of much less than 360 degrees is adequate to produce sufficient data for particle analysis of sample liquid 303 with particle analyzer sensor assembly 300. In some embodiments, a rotation of approximately 180 degrees is utilized although this number is quite arbitrary. That is, actuator 315 can repetitively rotate sample container holder 301 N degrees in a first (e.g., clockwise) direction and M degrees in a second (e.g., counterclockwise) direction to achieve an oscillatory motion about a central axis of sample container 302. The angular rotation rate and the total angle traveled will be dependent upon the viscosity of the liquid being measured and other factors such as measurement time, flex cable 323 length, or mechanical interferences.

FIG. 4A is a cross-sectional view that illustrates an embodiment of a liquid filled sample container 401 that can be used in conjunction with sample container holder 301 (shown in FIG. 3A). Sample container 401 is a container that is substantially transmissive to radiation 306 used for analytically probing the liquid therein. As shown in FIG. 4A, sample container 401 is modified to incorporate protuberances 402 in the bottom thereof, either by installation of inserts or by manufacturing sample container 401 to include protuberances within the wall material (e.g., glass or plastic structure) of the container 401 itself. Any number of protuberances can be formed in the bottom of sample container 401. In some embodiments, sample container 401 can be a glass vial. For example, suitable glass vials can include those used in the chemistry and medical fields, such as a modified 30 ml glass vial, PN/W224834, from Wheaton Industries Inc., 1501 North 10th Street, Millville, N.J. 08332 USA, but can also include any of a large number cylindrical containers of various diameters and lengths.

To improve measurement statistics in the particle analyzer, sample container 401 can include one or more protuberances 402 formed in the bottom of sample container 401 and offset from its center. In some embodiments, at least two protuberances are installed or formed in sample container 401. In the oscillatory operation of the sample container holder 301, protuberances 402 will cause the liquid sample to be continuously disrupted (e.g., stirred or otherwise agitated). Protuberances 402 not only produce a continuous exchange of dispersed particles 403 into the radiation probe volume 404, but the stirring action will also cause large particles 405 to remain in suspension. An additional effect of the stirring action caused by protuberances 402 is that liquid containing particles in the very center of sample container 401, which would otherwise have little motion relative to the radiation probe beam as a result of the oscillatory movement of the sample container 401 about its central axis, will instead demonstrate significant relative movement because of the continual disruption of the sample liquid from the rotating action of protuberances 402 with respect to the substantially stationary liquid as the container 401 is rotated back and forth.

Protuberances 402 can be installed into a purchased sample container that does not have protuberances in its bottom by any glass blower with ordinary skill at relatively low cost. Protuberances with a simple conical shape produce adequate stirring. As shown in FIG. 4B, shapes other than conical can be fabricated such as a wedge shape or a curved blade shape. These protrusions and others can easily be incorporated into the manufacturing of a vial if quantities are high enough to justify the engineering costs incurred. A sample container with a bottom cap assembly that contains a stirring blade assembly can also be fabricated. For example, FIG. 4C shows a sample container 431 with a bottom cap 436 and a stirring assembly 432. Bottom cap 436 can be of the screw type or it can be molded onto the bottom of sample container 431. Stirring can also be accomplished by inserting a cap with a stir bar assembly. For example, FIG. 4D shows a cap 440 with an attached rod 441 supporting a stir assembly 442.

FIG. 4E shows another embodiment of a sample container 451, where sample container 451 is capless and/or has a sufficiently large opening such that an insert can be securely installed into a flat or curved bottom of sample container 451. Insert 452 can have protuberances 454 of various shapes such as those shown in FIG. 4F. As shown in FIG. 4G, it is also possible to produce sample containers that have protuberances in both their bottoms and sides such as protuberances 462 in sample container 461. The protuberances 462 can have various shapes such as the shapes shown in FIG. 4H. Additionally the sample container needn't be strictly round. For example, sample containers suitable for use with embodiments of the particle analyzer sensor assembly 300 described above can also have shapes as shown in FIG. 4I, among others. As shown, embodiments of the particle analyzer sensor assembly 300 can utilize sample containers with a single flat side or sample containers that are hex or octal or any of a number of sides.

As shown in FIG. 3B, radiation that is scattered, reflected, diffracted, refracted, and/or radiated a particle in the probe volume is reflected from interior surface 301a of sample holder 301 and is received by detector 312. Detector 312 and associated electronics 317 can be carried on a printed circuit board (PCB) 322 that is attached to rotatable sample holder 301. Referring now to FIG. 5, radiation collected by detector 312 may be amplified by an electronic transimpedance amplifier 502. In some embodiments, a suitable transimpedance amplifier can be AD8610BRM which can be purchased from Analog Devices, Inc., One Technology Way, Norwood, Mass. 02062. The electronic signal is then passed through a low pass filter 503. In some embodiments, a suitable low pass filter is LT1564 which can be purchased from Linear Technology Corporation, 1630 McCarthy Blvd., Milpitas, Calif. 95035. The output of low pass filter 503 is supplied to an analog-to-digital converter (ADC) 504. In some embodiments, a suitable analog to digital converter is AD7685 which can be purchased from Analog Devices, Inc., One Technology Way, Norwood, Mass. 02062.

In embodiments, the above-described electronic circuits are mounted to the sensor PCB 322 (FIG. 3B) that is rigidly attached to rotatable sample holder 301. Electrical connection to PCB 322 mounted on sample container holder 301 can be accomplished by a variety of methods such as direct electrical connection, optical coupling, radio coupling, or the like. In some embodiments, a flexible cable (or simply "flex cable") 323 is used to connect the chassis-mounted PCB 506 containing receiving electronics and DC power to sensor PCB 322. For example, a suitable flex cable can be Molex 15166-0215 which can be purchased from Mouser Electronics, 1000 North Main Street, Mansfield, Tex. 76063. Flex cable 323 can supply digital signals from ADC 504 to circuits on PCB 506 to enable communication with a computing system 508. In embodiments, computing system 508 can be connected directly via a communication cable 507 (e.g., USB, Ethernet, serial or parallel connectors, fiber optic cables, and so forth), or by wireless (e.g., optical or radio frequency (RF)) communication protocols. In embodiments, computing system 508 includes one or more processors configured to receive electronic signals associated with the radiation received by detector 312; and determine one or more characteristics of particles within the liquid sample based upon the received electronic signals. For example, determinable characteristics can include particle size distributions, quantity, classifications, physical characteristics, and so forth. The electronic signals can be communicated via the communication cable 507 or by wireless communication from the receiver electronics on PCB 506 to computing system 508 for analysis.

Figure 6:
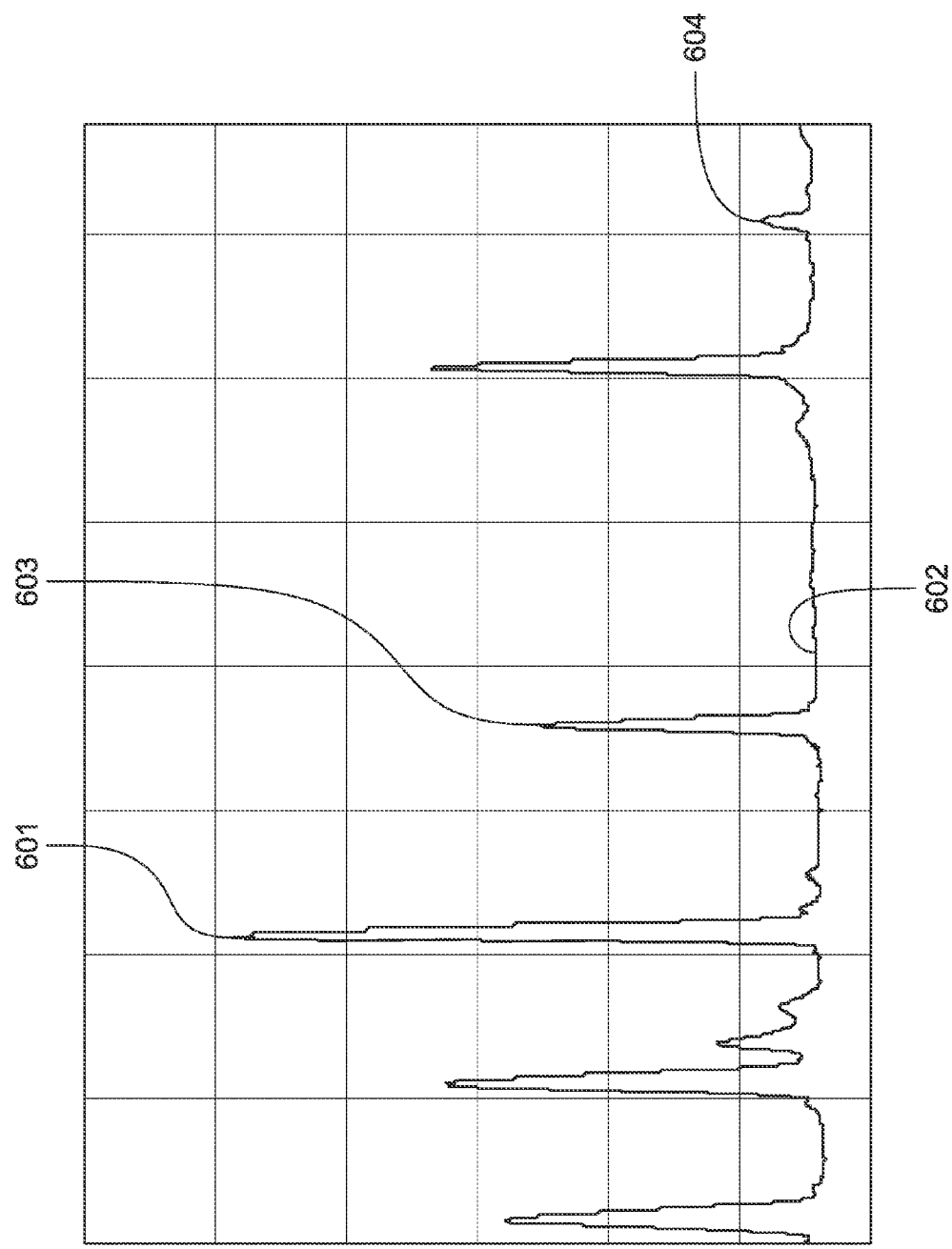
FIG. 6 shows an output voltage waveform of a detector of a particle analyzer constructed in accordance with an embodiment of the present disclosure.

The output signal of ADC 504 when returned to an analog signal and displayed as a time-dependent voltage output (e.g., as can be displayed by computing system 508) is shown in FIG. 6. Here signal pulses 601, 603 and 604 are representative detected scattering signals from single particles traversing radiation probe volume 404 (FIG. 4A). Baseline signal 602 is low in noise because all elements of the particle scanning system are stationary with respect to each other except the particle filled liquid within sample container 302. Frequency components of scattered radiation from all elements within the optical train such as the outside surface of sample container 302, beam directing element 309, apertures, and other surfaces are for the most part constant intensity radiation components, and as such, these constant intensity components can be removed by electronics or digital processing techniques that are well known in the art of signal processing. For example, these constant intensity components can simply be subtracted out as direct current (DC) values.

Example Process

Figure 7:
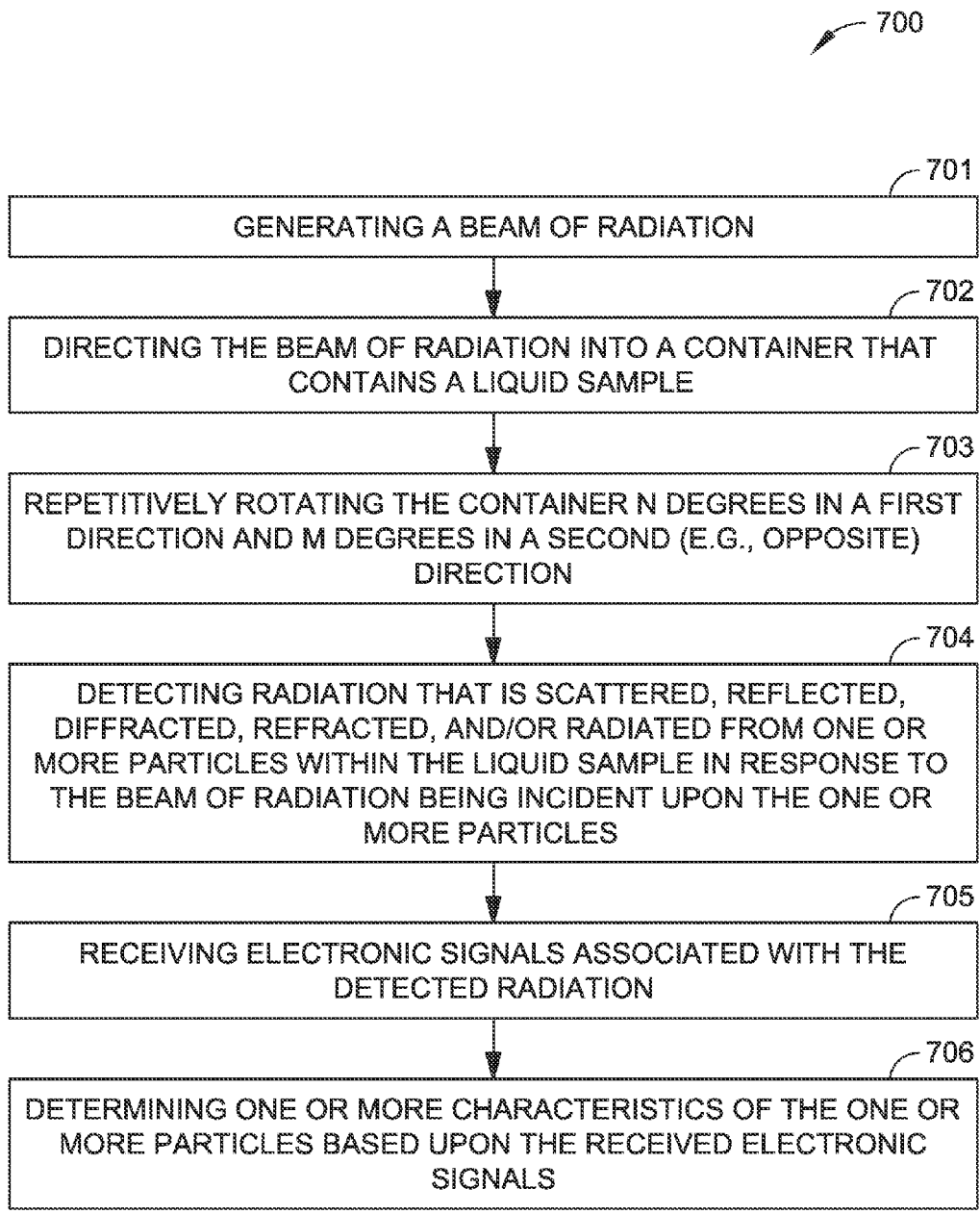
FIG. 7 is a flow diagram illustrating a method of analyzing particles in a liquid sample that can be implemented by a particle analyzer constructed in accordance with an embodiment of the present disclosure.

FIG. 7 shows a flow diagram for a method 700 of analyzing particles within a liquid sample. Method 700 can be performed by a particle analyzer, such as embodiments of particle analyzer 501 described herein. Accordingly, method 700 can include any steps or operations that are described herein with regard to particle analyzer 501 or that are necessary for achieving an attribute of particle analyzer 501 that is described herein. However, method 700 is in no way limited to any embodiment of particle analyzer 501 that is described herein. Method 700 can be performed by any system configured to carry out the steps or operations described below.

As shown in FIG. 7, method 700 can include the following operations: (701) generating a beam of radiation (e.g., with radiation source 305); (702) sending the beam of radiation into a container that contains a liquid sample (e.g., either directly from radiation source 305 or via one or more optical elements, such as element 309); (703) repetitively rotating the container N degrees in a first direction and M degrees in a second direction different from the first direction (e.g., oscillatory movement imparted by an actuator, such as actuator 315); (704) detecting radiation that is scattered, reflected, diffracted, refracted, and/or radiated from one or more particles within the liquid sample in response to the beam of radiation being incident upon the one or more particles (e.g., with detector 312); (705) receiving electronic signals associated with the detected radiation (e.g., with electronic circuitry 506 that is coupled to detector 312); and (706) determining one or more characteristics of the one or more particles based upon the received electronic signals (e.g., with computing system 508).

Those skilled in the art will appreciate that the forgoing steps can be carried out in any order, unless otherwise indicated herein, and that one or more steps may be carried out substantially simultaneously or at least partially in parallel. It should be further recognized that the various functions, operations, blocks, or steps described throughout the present disclosure may be carried out by any combination of hardware (e.g., optical, mechanical, or electronic), software, or firmware. Various steps or operations may be carried out by one or more of the following: electronic circuitry, logic gates, multiplexers, a programmable logic device, an applicationspecific integrated circuit (ASIC), a controller/microcontroller, or a computing system. A computing system may include, but is not limited to, a personal computing system, mainframe computing system, workstation, image computer, parallel processor, or any other device known in the art. In general, the terms "controller" and "computing system" are broadly defined to encompass any device having one or more processors, which execute instructions from a stored program on a carrier medium.

Program instructions implementing methods, such as those manifested by embodiments described herein, may be transmitted over or stored on carrier medium. The carrier medium may be a transmission medium, such as, but not limited to, a wire, cable, or wireless transmission link. The carrier medium may also include a non-transitory signal bearing medium or storage medium such as, but not limited to, a read-only memory, a random access memory, a memristor, ReRAM, a magnetic or optical disk, a solid-state or flash memory device, or a magnetic tape.

It is further contemplated that any embodiment of the disclosure manifested above as a system or method may include at least a portion of any other embodiment described herein. Those having skill in the art will appreciate that there are various embodiments by which systems and methods described herein can be implemented, and that the implementation will vary with the context in which an embodiment of the disclosure is deployed.

Furthermore, it is to be understood that the invention is defined by the appended claims. Although embodiments of this invention have been illustrated, it is apparent that various modifications may be made by those skilled in the art without departing from the scope and spirit of the disclosure.

What is claimed is:

1. A system for analyzing particles in a liquid sample, the system comprising:
   a holder configured to rigidly secure a container that contains a liquid sample;
   an actuator configured to repetitively rotate the holder N degrees in a first direction and M degrees in a second direction different from the first direction, wherein N and M are real numbers greater than zero;
   a radiation source configured to generate a beam of radiation, the radiation source being rigidly attached to the holder, the beam of radiation being directed through the container into the liquid sample; and
   a detector configured to receive radiation that is at least one of scattered, reflected, diffracted, refracted, or radiated from one or more particles within the liquid sample in response to the beam of radiation being incident upon the one or more particles.

2. The system of claim 1, further comprising a processor configured to:
   receive electronic signals associated with the radiation received by the detector; and
   determine one or more characteristics of the one or more particles based upon the received electronic signals.

3. The system of claim 1, wherein the holder includes an output aperture that enables the beam of radiation to exit an interior region of the holder after the beam of radiation has traveled through the container.

4. The system of claim 3, further comprising a beam dump configured to receive the beam of radiation after the beam of radiation has traveled through the output aperture.

5. The system of claim 1, wherein the radiation source is rigidly attached to an interior region of the holder.

6. The system of claim 1, wherein the radiation source is rigidly attached to an exterior region of the holder, and wherein the holder includes an input aperture that enables the beam of radiation to enter an interior region of the holder.

7. The system of claim 1, wherein rotation of the holder causes the container to rotate about a substantially central axis of the container.

8. The system of claim 7, wherein N is less than or equal to 360 degrees, and M is less than or equal to 360 degrees.

9. The system of claim 1, wherein the holder includes one or more inner surfaces with suitable reflectance for causing radiation that is at least one of scattered, reflected, diffracted, refracted, or radiated from the one or more particles within the liquid sample to be redirected within the holder until the radiation is received by the detector.

10. The system of claim 9, wherein the one or more inner surfaces of the holder define a substantially cylindrical volume.

11. The system of claim 1, wherein the container includes one or more protuberances configured to disrupt the sample liquid when the container is rotated.

12. The system of claim 1, wherein the container comprises a substantially cylindrical container.

13. The system of claim 1, further comprising at least one optical element configured to direct the beam of radiation from the radiation source into the container.

14. The system of claim 1, wherein the actuator is configured to repetitively rotate the holder N degrees in the first direction and M degrees in the second direction according to a rotation reversal rate in the range of approximately 0.01 to 10 seconds.

15. A method of analyzing particles in a liquid sample, the method comprising:
   directing a beam of radiation from a radiation source into a container that contains a liquid sample;
   repetitively rotating the container N degrees in a first direction and M degrees in a second direction different from the first direction, wherein N and M are real numbers greater than zero; and
   detecting radiation that is at least one of scattered, reflected, diffracted, refracted, or radiated from one or more particles wherein the container is rigidly secured by a holder and the radiation source is rigidly attached to the holder within the liquid sample in response to the beam of radiation being incident upon the one or more particles.

16. The method of claim 15, further comprising:
   receiving electronic signals associated with the detected radiation; and
   determining one or more characteristics of the one or more particles based upon the received electronic signals.

17. The method of claim 15, wherein the container is rotated about a substantially central axis of the container.

18. The method of claim 15, wherein N is less than or equal to 360 degrees, and M is less than or equal to 360 degrees.

19. The method of claim 15, wherein the container is repetitively rotated N degrees in the first direction and M degrees in the second direction according to a rotation reversal rate in the range of approximately 0.01 to 10 seconds.

* * * * *